(12) United States Patent
Stenflo et al.

(10) Patent No.: US 7,439,025 B2
(45) Date of Patent: Oct. 21, 2008

(54) ANTIBODIES BINDING A GAMMA CARBOXYGLUTAMIC ACID DISPLAYING EPITOPE

(75) Inventors: Johan Stenflo, Malmö (SE); Loisa Mary Stenberg, Malmö (SE); Mark Alan Brown, Malmö (SE)

(73) Assignee: Protease AB, Malmo (SE)

( * ) Notice: Subject to any disclaimer, the term of this patent is extended or adjusted under 35 U.S.C. 154(b) by 522 days.

(21) Appl. No.: 10/220,548

(22) PCT Filed: Mar. 1, 2001

(86) PCT No.: PCT/SE01/00430

§ 371 (c)(1), (2), (4) Date: Jan. 9, 2003

(87) PCT Pub. No.: WO01/64748

PCT Pub. Date: Sep. 7, 2001

(65) Prior Publication Data

US 2003/0138844 A1 Jul. 24, 2003

(30) Foreign Application Priority Data

Mar. 2, 2000 (SE) .................... 0000675

(51) Int. Cl.
*C07K 16/18* (2006.01)
*C07K 1/22* (2006.01)
*G01N 33/543* (2006.01)
*G01N 33/573* (2006.01)
*G01N 33/577* (2006.01)

(52) U.S. Cl. ............ 435/7.1; 435/7.21; 435/7.4; 435/7.9; 435/7.92; 435/69.6; 435/70.21; 436/518; 436/530; 436/547; 436/548; 530/387.9; 530/413

(58) Field of Classification Search ............ 435/7.1, 435/7.21, 7.4, 7.9, 7.92, 69.6, 70.21; 436/518, 436/530, 547, 548; 530/413
See application file for complete search history.

(56) References Cited

U.S. PATENT DOCUMENTS 5,229,490 A * 7/1993 Tam ............... 530/324

6,379,975 B1 * 4/2002 Linse et al. ............ 436/501
6,624,295 B1 * 9/2003 Adams et al. .......... 536/23.53
2003/0138844 A1 * 7/2003 Stenflo et al. ............ 435/7.1

FOREIGN PATENT DOCUMENTS

| DE | 4008546 A1 * | 9/1990 |
| EP | 0 645 630 | 3/1995 |
| WO | WO 94/08615 | 3/1994 |
| WO | WO 99/09058 | 2/1999 |

OTHER PUBLICATIONS

Roitt, Essential immunology, 5th ed., Blackwell Scientific Publications, 1984, pp. 6-8.*
Brown, et. al., 2000, "Identification and Purification of Vitamin-K dependent Proteins and Peptides with Monoclonal Antibodies Specific for γ-Carboxyglutamyl (Gla) Residues." *J. of Biol Chem.* 275(26):19795-19802.
Eguchi et al., 1999, "Sandwich immunoassay specific for he N-terminal sequence of osteocalcin." *J. Immunol. Methods.* 184:231-240.
Koyama et al., 1991, "A one step sandwich enzyme immunoassay for γ-carboxylated osteocalcin using monoclonal antibodies." *J. of Immunol. Methods.* 139:17-23.
Tam, 1988, "Synthetic peptide vaccine design: synthesis and properties of a high-density multiple antigenic peptide system." *Proc. Natl. Acad. Sci.* 85(15):5409-5413.
TaKaRa Bio, Inc., TaKaRa Biotechnology Catalog on-line for "Gla-type Osteocalcin (Gla-OC)/Undercarboxylated Osteocalcin (Glu-OC) EIA kit (Precoated)" (visited Feb. 5, 2007) http://bio.takara.co.jp/bio_en/Catalog_d.asp?C_ID=C0463.

* cited by examiner

*Primary Examiner*—David A Saunders
(74) *Attorney, Agent, or Firm*—Jones Day

(57) ABSTRACT

Antibodies are described, which are suitable for identification of γ-carboxyglutamic acid (Gla), said antibodies having an ability of identifying Gla residues in proteins and/or peptides, while not reacting with glutamic (Glu) residues in corresponding proteins and/or peptides. Methods for the preparation and identification of said antibodies as well as methods for detection of Gla in biological fluids, tissue extracts, tissue specimens, in which methods said antibodies are used, are also described. There is also described the use of said antibodies for immunopurification of Gla-containing proteins or peptides by, for instance, immunoprecipitation or immunoaffinity chromatography.

32 Claims, 5 Drawing Sheets

Figure 1:
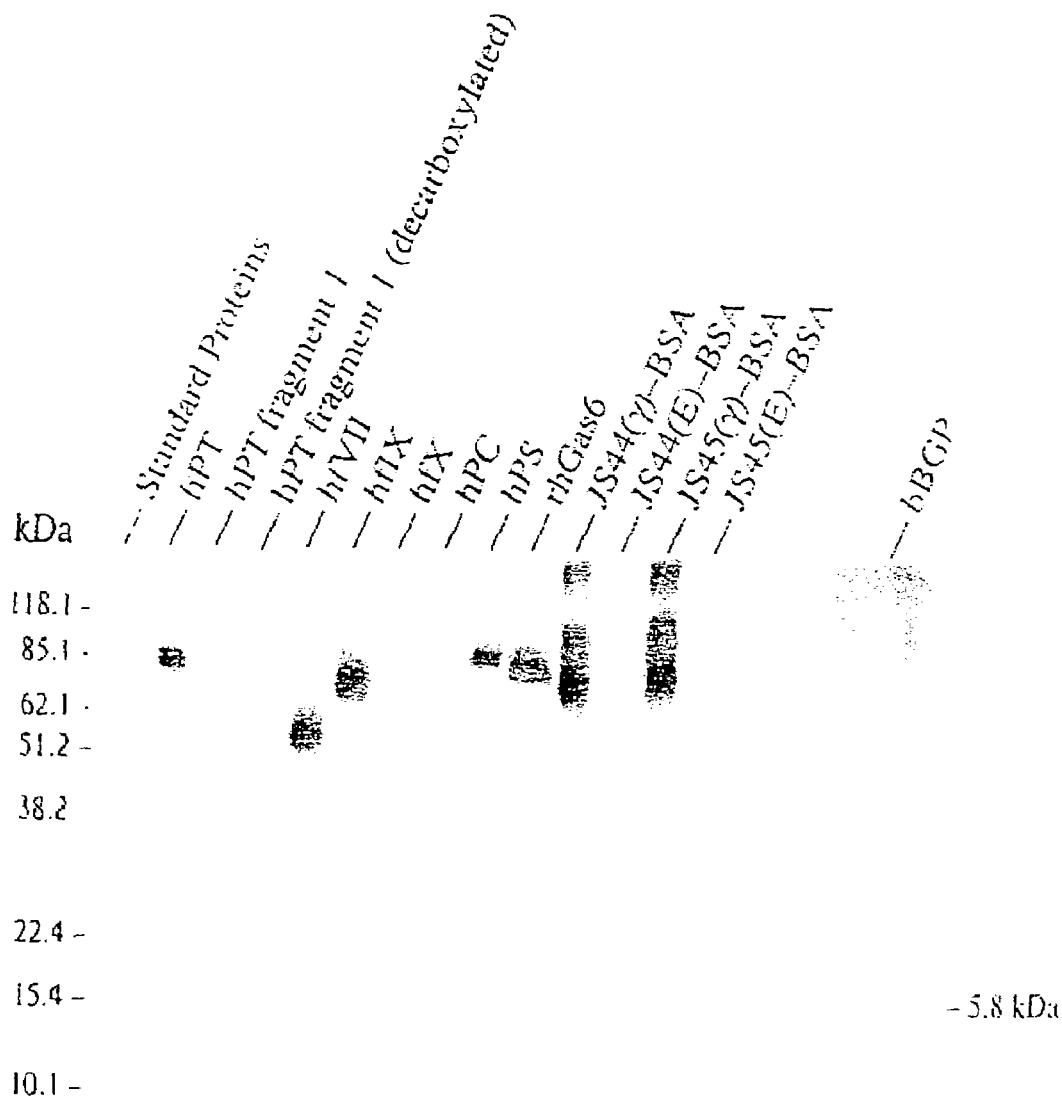

A.

B.

C.

ANTIBODIES BINDING A GAMMA CARBOXYGLUTAMIC ACID DISPLAYING EPITOPE

FIELD OF THE INVENTION

The present invention relates to antibodies for the detection of γ-carboxyglutamic acid (Gla), methods for the preparation and identifying of said antibodies and methods for the detection of Gla in biological fluids, tissue extracts, tissue specimens and the like wherein said antibodies are utilised. The invention also relates to the use of antibodies of this type for the immunopurification of Gla-containing proteins by, for instance, immunoprecipitation or immunoaffinity chromatography.

BACKGROUND OF THE INVENTION

Gla is an unusual amino acid formed by γ-carboxylation of a limited number of glutamic acid (Glu) residues in certain proteins. Carboxylation, which is an early posttranslational event, requires vitamin K and the presence of Gla in proteins/peptides has so far always been associated with the action of vitamin K (Furie et al., 1999; Suttie, 1985).

Carboxylation is catalysed by a vitamin K-dependent carboxylase, an enzyme that has been purified and cloned. The complementary DNA has been expressed and the recombinant protein found to be fully active. An unstable metabolite of vitamin K, derived from the hydroquinone form of the vitamin, is involved in the abstraction of a proton from the γ-carbon atom of certain peptide-bound Glu residues with subsequent incorporation of $CO_2$ and formation of Gla, a malonic acid derivative. Typically, Gla-containing proteins have an N-terminal portion termed the propeptide that is recognised by the carboxylase. Following carboxylation and release of the modified protein from the enzyme the propeptide is removed by limited proteolysis.

Proteins that contain Gla are often referred to collectively as the 'vitamin K-dependent proteins' (Stenflo and Dahlbäck, 1994). Among these proteins the hemostatic factors that require vitamin K for normal synthesis have been studied in most detail. They comprise prothrombin (factor II), factor VII, factor IX, factor X and the two regulatory proteins, protein C and its cofactor protein S.

Structurally related to factors VII, IX, X and protein C is protein Z that, according to recent investigations, may be involved in the regulation of blood coagulation.

Homologues to the proteins of this group have been found in numerous vertebrates including snakes, e.g. the venom of the toxic snake *Tropidechis carinatus* contains a protein that resembles factor X both in terms of structure and biological activity (Joseph et al., 1999). Growth arrest-specific protein 6 (Gas6) is a homologue of protein S that seems to be involved in apoptosis.

The Gla-containing hemostatic factors and their homologues all have an amino-terminal (N-terminal) Gla domain of approximately 45 amino acid residues in which all 9-12 Glu residues contained therein are normally carboxylated to Gla. The propeptide, which is encoded on the same exon as the N-terminal part of the Gla domain, is recognised by the vitamin K-dependent carboxylase and activates the enzyme. After binding its substrate, the carboxylase seems to carboxylate all Glu residues in the vicinity of the propeptide (i.e. up to about residue +45 in the vitamin K-dependent hemostatic factors) irrespective of the surrounding amino acid sequence.

The vitamin K-dependent coagulation factors are primarily synthesised in the liver and can be divided into three groups depending on their domain structure. Factors VII, IX and X and protein C have an N-terminal Gla domain that is followed by two domains that are homologous to the epidermal growth factor (EGF) whereas the C-terminal part of the molecule is occupied by a serine proteinase domain. Another homologue, protein Z, also has this domain structure. However, natural mutations in the protein Z gene have altered the active site residues of the protein and it has no proteinase activity. Prothrombin also has an N-terminal Gla domain that is followed by a characteristic loop, two so called kringle domains, and a serine proteinase domain. Protein S and Gas6 are homologues. In protein S, the region that follows the Gla domain contains one or two peptide bonds that are particularly sensitive to thrombin. This region is followed by four EGF-like domains, whereas the C-terminal half of the molecule is homologous to a sex steroid-binding protein in human plasma.

The vitamin K-dependent proteins that are involved in blood coagulation and its regulation are, with the exception of protein S and protein Z, proenzymes of serine proteinases. Although the enzymes have full activity against substrates with small molecular masses (e.g. short peptides), their activity is minimal against their physiological substrate(s) (for factor VIIa these are factors IX and X; for factor IXa, factor X; for factor Xa, prothrombin; the 'a' in VIIa and so forth denotes the enzymatically active form of the protein) unless they are in complex with their appropriate membrane-bound cofactor, thus forming enzymatically active membrane-bound macromolecular complexes. The enzyme in the complex, for example factor Xa in complex with its cofactor, factor Va (here the 'a' denotes the active form of the cofactor to distinguish it from the inactive pro-cofactor) activates its substrate, prothrombin, by limited proteolysis.

The nine to twelve Gla residues in the Gla domain mediate binding of 7-10 calcium ions which is crucial to keep the Gla domain in the conformation that is required for biological activity and hence for its interaction with biological membranes.

Clinically used anticoagulant drugs such as Warfarin® function by inhibiting Gla formation in the vitamin K-dependent proteins, thus reducing the calcium affinity of the protein and its affinity for biological membranes. Such drugs are used, for instance, in the treatment of venous thrombosis and pulmonary embolism.

Gla has also been found in two proteins in mineralised tissues; bone Gla protein (or osteocalcin) and matrix Gla protein. These proteins are smaller than the coagulation factors and contain fewer Gla residues. However, they have structures resembling the propeptide that are crucial for substrate recognition by the vitamin K-dependent carboxylase. These carboxylations have also been shown to have an obligatory requirement for vitamin K. Bone Gla protein is involved in the regulation of calcification of mineralised extracellular matrices and matrix Gla protein seems to have a broad role in calcium homeostasis.

In addition to coagulation factors and the two proteins found in mineralised tissues, the presence of Gla has been reported in several proteins in urine, kidney, placenta, the chorioallantoic membrane of chicken eggs and so forth but in most cases these proteins have not been characterised in molecular detail (Vermeer and De Boer-Van den Berg, 1985).

More recently, the cDNA of two putative membrane proteins with typical Gla domains (hence resembling the coagulation factors) were cloned (Kulman et al., 1997). The function of these proteins is not yet known nor have they been characterised at the protein level.

The discovery of Gla in the venom of predatory snails of the genus *Conus* and the finding that vitamin K is involved in its biosynthesis in these molluscs indicates that vitamin K presumably has important functions in many more biological systems than hitherto assumed (Olivera et al., 1990). Moreover, the biological activity of a *Conus*-derived toxin was shown to depend on the presence of Gla, i.e. a synthetic toxin with the same structure except that Gla had been substituted with Glu was biologically inactive.

From the above it should be obvious that the identification of Gla in proteins is of considerable interest, and that this interest is rapidly increasing as a result of recent discoveries implicating Gla in the function of novel proteins with important biological functions. This field of research would be much simplified were there rapid, simple, dependable and inexpensive methods to identify Gla in proteins.

The standard method for the identification and quantification of amino acids has been amino acid analysis after acid hydrolysis. However, this method is unsuitable for the identification of Gla as it is a malonic acid derivative and hence is decarboxylated to Glu by acid hydrolysis. Therefore, alkaline hydrolysis has been used to quantify Gla in proteins. Although suitable for quantification of Gla in purified proteins, this method is of limited use for the identification of Gla-containing proteins in biological fluids or tissue extracts.

As the Gla-containing proteins that have been studied in detail have been found to bind calcium, 'calcium blotting' has sometimes been used to identify Gla-containing proteins. The method entails SDS-polyacrylamide gel electrophoresis followed by transfer to a suitable membrane (e.g. nitrocellulose membrane) that is then incubated in a buffer containing a radioactive calcium isotope ($^{45}Ca$). After drying and exposure of the membrane to a suitable film or detector, the calcium-binding protein(s) can often be identified. The weaknesses of the method are that it does not discriminate between Gla-containing and other calcium-binding proteins and it is not quantitative. Moreover, a high calcium affinity is required for the protein to be detected. Finally, the method requires the protein to retain a native, calcium-binding conformation despite having been exposed to SDS.

Colourimetric methods for the detection of Gla-containing proteins have been devised but they have not been widely used (Jie et al., 1995; Nishimoto, 1990).

During protein/peptide sequencing (using Edman chemistry) Gla is easily identified after chemical modification (Cairns et al., 1991). However, this requires homogeneous proteins and should be preceded by a quantitative Gla measurement of an alkaline hydrolysate of the protein.

Mass spectrometry is an indispensable method for the characterisation of homogeneous Gla-containing proteins/peptides (e.g. Rigby et al., 1999). However, despite its merits, mass spectrometry is not suitable for the detection of Gla-containing proteins in biological fluids or tissue extracts.

A simple immunochemical method for the detection of Gla in biological fluids and tissue specimens is needed, as well as a simple method for the affinity purification of Gla-containing proteins. Such a method would lead to new advances in research relating to vitamin K-dependent proteins and would also be of considerable use in the purification of therapeutically useful recombinant vitamin K-dependent proteins such as coagulation proteins. Such methods have been devised for the simple identification and purification of proteins containing phosphorylated tyrosine, serine and threonine residues and have turned out to be very useful (e.g. Frackelton et al., 1983).

DESCRIPTION OF THE INVENTION

The present invention relates to a set of antibodies, monoclonal as well as polyclonal, that are suitable for the identification of Gla in proteins and/or peptides. Characteristic properties of the antibodies are:

They have an ability to identify Gla residues, both a single residue, pairs of Gla residues or multiple Gla residues in proteins and peptides.

The antibodies do not react with the corresponding proteins/peptides that contain Glu rather than Gla.

The antibodies according to the present invention are obtainable by immunisation of an animal with a synthetic peptide complex synthesised according to a published procedure (Tam, 1988). The peptide contains single Gla residues and pairs of Gla residues in sequences that are otherwise random (Table 1).

The antibodies are also obtainable by immunisation of an animal with one or more Gla residues or other malonic acid derivative attached to a peptide, protein or other polymer.

Animals suitable for the above immunisation methods are mice (preferably Balb/c mice), rats, rabbits, horses, cows, goats, chicken and sheep and other species.

A further preparation method is by the de novo design and production of antibodies, e.g. Fab or single chain Fv antibodies, by recombinant DNA techniques, including phage, bacteria or ribosome display methods.

All preparation methods include screening for and isolation of said antibodies.

Monoclonal antibodies are produced using standard methods (Borrebäck and Eylar, 1981). To test the cell clones producing antibodies, ELISA (enzyme-linked immunosorbent assay)-type assays are used. These assays employ the synthetic peptides that contain either Gla or Glu for the selection of clones with the desired properties (Table 1). In addition, vitamin K-dependent coagulation factors are used for the identification of appropriate antibody-producing clones. Clones producing antibodies with desired properties are expanded and antibodies produced either as ascetic fluid in mice or by tissue culture.

Polyclonal antisera may be produced in animals using well-known methods. The antibodies of interest are isolated by e.g. sequential adsorption of the antiserum on immobilised peptides containing either Gla or Glu. The isolated antibodies are tested with prothrombin, factor IX and factor X using western blotting.

The antibodies produced according to the present invention are suitable for:

1) The identification of Gla-containing proteins in biological fluids or tissue extracts by, for instance, western blotting.
2) The identification of Gla-containing proteins in tissue sections by immunohistochemistry.
3) Quantitative measurements of Gla-containing proteins/peptides in so called sandwich assays of, for instance, the ELISA or DELFIA® type.
4) Quantitative measurements of Gla-containing proteins to monitor the degree of carboxylation of, for instance, vitamin K-dependent coagulation factors, for instance factor X, during treatment of patients with vitamin K-antagonistic drugs such as Warfarin®.
5) Purification of Gla-containing proteins from biological fluids or tissue extracts by, for instance, immunoaffinity chromatography or immunoprecipitation.
6) Purification of recombinant Gla-containing proteins from lysed cells or cell culture media by, for instance, immunoaffinity chromatography or immunoprecipitation.

7) Fractionation of recombinant Gla-containing proteins according to their Gla content by immunoaffinity chromatography. Elution of adsorbed proteins from immunoaffinity columns, typically in a Tris buffer at or near physiological pH, can in certain instances be made by the addition of metal ions, such as calcium ions, e.g. added in the form of $CaCl_2$, to the buffer, whereas in other instances other means for elution are required, for instance, a change in the pH or the use of chaotropic agents.
8) Probing the conformation of Gla domains and the influence of calcium and other ions on the conformation.

Ad. 1) In western blotting experiments, the detection of Gla-containing proteins/peptides in biological fluids or tissue extracts can be performed with the label (such as an enzyme or a fluorescent or a radioactive compound) covalently attached to the primary antibody or by use of a so called secondary antibody to which an enzyme or other label has been covalently linked. Suitable enzymes include alkaline phosphatase or horse radish peroxidase. Detection can also be made by chemiluminescence or similar methods. Western blotting can be used to identify Gla in the so called Gla domain of coagulation factors and in proteins with homologous Gla domains. After decarboxylation of Gla to Glu the antibodies do not react with the proteins. The method also allows for the identification of Gla in Gla-containing proteins or peptides that do not have typical so called Gla domains. Examples of such proteins are the so called bone Gla protein (osteocalcin) and matrix Gla protein as well as Gla-containing proteins/peptides from the venom of molluscs of the genus *Conus*.

Ad. 2) The antibodies can be used to identify Gla in a tissue section by, for instance, immunohistochemistry. They can also be used to identify Gla-containing proteins, integral membrane proteins or intracellular proteins in cultured cells by immunohistochemistry or FACScan methods. These methods can be performed with the label (such as an enzyme or a fluorescent or a radioactive compound) attached to the primary antibody or by use of a so-called secondary antibody.

The invention is further illustrated by the following non-limiting examples together with the figures.

EXAMPLES

Peptide Synthesis and Conjugation of Peptides to Bovine Serum Albumin:

Peptides were synthesised on a Milligen 9050 Plus peptide synthesiser (Perkin Elmer Corp., Stockholm, Sweden). The peptide synthesis was made with DPfp Fmoc amino acids from PerSeptive Biosystems (Framingham, Mass., USA). The peptide complex used for immunisation was synthesised using the multiple antigen peptide (MAP) system of Tam (1988) and the amino acid residues around Gla residues were varied (see JS30 in Table 1).

Immunisations were made as described below. Peptides used for testing the antibodies were synthesised with a C-terminal Cys residue and conjugated to bovine serum albumin via the Cys residues using established procedures.

Production of Gla-Specific Rabbit Polyclonal Antibodies:

The ability of the synthetic JS30 peptide complex (Table 1) to elicit the production of Gla-specific polyclonal antibodies was tested by immunising rabbits according to standard procedures. Four subcutaneous immunisations were given over a period of four months, each with 1 mg of the peptide complex emulsified in Freund's complete adjuvant. Serum from test bleedings was analysed by western blotting for crossreactivity against prothrombin, factor IX and factor X. After an adequate immune response was obtained, serum was diluted 1:1 with 154 mM NaCl and the immunoglobulin fraction was precipitated by adding ammonium sulfate to 45% saturation. The precipitate was isolated by centrifugation and dialysed against 50 mM Tris-HCl/0.1 M NaCl, pH 7.5. Gla-specific antibodies were then isolated by peptide-affinity chromatography by employing synthetic peptides that contained single and paired Gla residues (JS31 peptide) or Glu residues (JS32) at the corresponding positions (Table 1). Each peptide was covalently attached via its C-terminal cysteine residue to thiopropyl-Sepharose (Amersham Pharmacia Biotech AB, Uppsala, Sweden) according to the resin manufacturer's instructions. The dialysed immunoglobulin preparation was chromatographed on a column made from the JS32-conjugated resin to remove antibodies that bound to the Glu-containing peptide. The flowthrough fraction (protein that did not bind to the column) was then chromatographed on a column made from the JS31-conjugated resin to isolate Gla-specific antibodies. The column was washed and bound antibodies were eluted with a low pH buffer, dialysed into 50 mM Tris-HCl/0.1 M NaCl, pH 7.5, and stored at −20° C.

The isolated antibodies were tested by western blotting to assess their crossreactivity against factor IX, factor X, prothrombin and prothrombin fragment 1 (a fragment comprising residues 1-156 including the Gla domain). The antibodies recognised all four proteins, demonstrating that apparently Gla-specific polyclonal antibodies had been produced. The degree of crossreactivity was greatly enhanced if disulfide bonds in the antigens had been reduced prior to electrophoresis to further disrupt the native structure of the Gla domain. These antibodies were not tested in further detail.

Production of Monoclonal Antibodies:

Balb/c mice were immunised with the synthetic peptide complex (Table 1). Each mouse was immunised with 10 μg of said peptide complex each time. The first immunisation was made intracutaneously with the peptide emulsified in Freund's complete adjuvant (Difco Laboratories, Detroit, Mich., USA) and the second and third ones were made subcutaneously with Freund's incomplete adjuvant. After testing the immune response, two additional immunisations were made, each time with 50 μg peptide complex per mouse in Freund's incomplete adjuvant.

The mouse plasma was tested using an ELISA with the appropriate peptide (Table 1) conjugated to bovine serum albumin. Tests were also made with bovine prothrombin and with a proteolytic fragment of bovine factor X that consists of the Gla domain linked to the N-terminal EGF-like domain (Persson et al., 1989). Proteins and peptide conjugates were coated in 96-well microtiter plates. A good antibody response was obtained after four to five months. Four, three, two and one day prior to cell fusion, each mouse was injected intraperitoneally with approximately 200 μg of the same immunogen (without an adjuvant). For cell fusion, the cells were extracted and fused with the myeloma cell line SP2/-AG14 using 45% polyethylene glycol 1540 and 7% DMSO (dimethyl sulfoxide) under standard conditions (Borrebäck and Eylar, 1981). Fused cells in DMEM medium supplemented with HAT (hypoxanthine, aminopterin, thymidine) were seeded into 96-well microtiter plates at a cell density of approximately $10^5$ cells per well together with approximately $10^4$ feeder cells per well. After about ten days hybridoma supernatants were screened for antibody production.

Clones producing antibodies with interesting properties were identified as described below. The hybridomas were subcloned twice by the limiting dilution method using 96-well plates (0.5 to 1.0 cell per well) using mouse peritoneal macrophages as feeder cells. Stable clones producing monoclonal antibodies of interest were grown to high cell density and injected (0.2 ml per mouse) intraperitoneally into pristane-primed mice for antibody production. Antibodies were also produced on a preparative scale by tissue culture using a Technomouse apparatus (Integra Biosciences). The cell lines were preserved frozen in 95% fetal bovine serum and 5% DMSO in liquid nitrogen.

The procedure for the identification of clones producing antibodies that were specific for Gla-containing peptides/proteins was carefully designed. Microtiter plates were coated with the appropriate protein, protein fragment or peptide-bovine serum albumin conjugate in 0.1 M carbonate buffer, pH 9.6 (0.5 µg per well). The peptides used in the tests are shown in Table 1. After washing, unoccupied binding sites in the wells were "blocked" by adding a solution of bovine serum albumin (10 mg/ml, 100 µg/well) in 50 mM Tris-HCl/0.1 M NaCl, pH 7.4 and incubating the plates for 15 min. After washing, culture medium was added to identify antibody producing clones. After again washing the wells, a peroxidase-conjugated rabbit anti-mouse immunoglobulin (DAKO A/S, Glostrup) was added. Clones of interest were identified by comparing the antibody reactivity observed with peptides containing Gla to the reactivity observed with the corresponding peptide containing Glu instead of Gla (in both cases the peptides were conjugated to bovine serum albumin).

Purification of Anti-Gla Monoclonal Antibodies:

The 16 anti-Gla monoclonal antibodies were each purified from mouse ascites or conditioned mouse hybridoma cell culture medium using affinity chromatography on protein G-coupled resin. All solutions were prepared using highly purified reagents and highly purified water. Approximately 50 ml of the antibody-containing solution was passed through a 0.45 µm filter, then diluted 1:1 with IgG Binding Buffer (0.1 M sodium acetate buffer/150 mM NaCl, pH 5.0) and loaded at a flow rate of 1 ml/min onto a 5-ml HiTrap™ Protein G column (Amersham Pharmacia Biotech AB, Uppsala, Sweden) that had been pre-equilibrated with IgG Binding Buffer. After loading, the column was washed with IgG Binding Buffer at a flow rate of 3 ml/min until the absorbance at 280 nm neared the baseline level. Antibody that had bound to the column was eluted with 0.1 M glycine-HCl, pH 2.7 at a flow rate of 3 ml/min and the eluate collected into a tube containing 1 M Tris-HCl buffer, pH 9.0 (1 ml of the buffer for each 9 ml eluate). NaCl was added to the eluate to a final concentration of 0.5 M and the antibody was dialysed into 20 mM Tris-HCl/0.5 M NaCl, pH 7.4 and concentrated. The concentration of the purified antibody was determined using an Easy Titer® Mouse IgG Assay Kit (Pierce Chemical Co., Rockford, Ill., USA) and ImmunoPure® mouse immunoglobulin G (IgG) (Pierce) as the standard protein, according to the manufacturer's instructions. Each of the 16 purified monoclonal antibodies appeared to be homogeneous when resolved by discontinuous SDS-PAGE according to the method of Laemmli (1970). The purified monoclonal antibodies were stored at −20° C. before use.

The characteristics of each of the 16 purified anti-Gla antibodies were examined by several methods and based on these analyses the antibodies could be classed into seven distinct groups (Table 2).

Western Blot Analysis of Monoclonal Antibodies:

All solutions were prepared using highly purified reagents and highly purified water. Purified (plasma-derived) samples of human factor VII (hfVII), human factor IX (hfIX), activated human factor IX (fIXa), human factor X (hfX), human protein C (hPC), human protein S (hPS) and bovine bone Gla protein (bBGP) were purchased from Haematologic Technologies, Inc. (Essex Junction, Vt., USA). Lyophilised venom from the tiger snake (*Notechis scutatus scutatus*), the taipan snake (*Oxyuranus scutellatus*) and the red-bellied black snake (*Pseudechis porphyriacus*) were purchased from Sigma Chemical Co. (St. Louis, Mo., USA). Purified recombinant activated human fVII (rhfVIIa) was a gift from Novo Nordisk (Copenhagen, Denmark). Purified samples of hfIX, hPC, human prothrombin (hPT), hPT fragment 1, and decarboxylated hPT fragment 1 were prepared in the laboratory by standard procedures (Bajaj and Birktoft, 1993; Bajaj et al., 1982; Price 1984). Conditioned cell culture containing ~5 µg/ml recombinant human growth arrest-specific protein 6 (rhGas6) was dialysed into 20 mM Tris-HCl/154 mM NaCl, pH 7.4 (i.e. Tris-buffered saline; TBS) and concentrated before use. In some cases protein concentrations were determined by amino acid analysis using standard procedures, otherwise they were determined spectrophotometrically or the concentration stated by the manufacturer was used. BENCHMARK™ Prestained Protein Ladder was purchased from Life Technologies, Inc. (Täby, Sweden). Nitro Blue Tetrazolium (2',2'-di-p-nitrophenyl-5,5'-diphenyl-3,3'-[3,3'-dimethoxy-4,4'-diphenylene]ditetrazolium chloride) (i.e. NBT) and 5-bromo-4-chloro-3-indolyl phosphate (BCIP) were purchased from Sigma Chemical Co. (St. Louis, Mo., USA).

Protein samples were denatured and reduced and resolved in SDS/12% or 15% (w/v) polyacrylamide gels by the method of Laemmli (1970). After electrophoresis the gels were equilibrated in Transfer Buffer (10 mM 3-(cyclohexylamino)-1-propane-sulfonic acid, pH 11/10% (v/v) methanol) for 10 min and the proteins electroblotted to Problott™ membrane (Applied Biosystems, Inc., Stockholm, Sweden) in Transfer Buffer at a constant voltage of 50V for 90-120 minutes. Unoccupied binding sites were blocked by incubating the membrane in TBS containing 10% (w/v) skim milk powder for 2 hours with gentle shaking. The membrane was then rinsed briefly with TBS containing 0.2% (v/v) Tween 20 (i.e. TBS/T) and incubated with purified monoclonal antibody (5 µg/ml in TBS/T) for 60 minutes at room temperature with gentle shaking. The membrane was washed with TBS/T (two times for 1 minute each followed by four times for 5 minutes each) and incubated with gentle shaking for 30 min at room temperature with alkaline phosphatase-conjugated rabbit anti-mouse IgG (DAKO A/S, Glostrup, Denmark) that had been diluted 1:1000 in TBS/T. The membrane was washed with TBS/T (two times for 1 minute each followed by four times for 5 minutes each) and developed by incubation in 10 ml 100 mM Tris-HCl, pH 9.5/100 mM NaCl/5 mM $MgCl_2$ to which had been added 66 µl NBT solution (50 mg/ml in 70% (v/v) dimethylformamide) and 33 µl BCIP solution (50 mg/ml in dimethylformamide). Colour development was terminated by rinsing the membrane with 0.25 M ethylenediamine tetraacetic acid (EDTA), pH 7.4.

As an example, the results obtained with monoclonal antibody M3B are shown in FIG. 1 and demonstrate that the antibody is able to bind a wide range of immobilised Gla-containing polypeptides under western blotting conditions. Results for each of the seven groups of anti-Gla monoclonal antibodies are given in Table 3.

A hybridoma cell line M3B that produces the monoclonal antibody M3B was deposited on Dec. 20, 2006 with an International Depository Authority, DSMZ, the German resource center for biological material, located at Inhoffenstraβe 7B, 38124 Braunschweig, GERMANY, in compliance with the Budapest Treaty on the International Recognition of the Deposit of Microorganisms for the Purposes of Patent Procedure. The hybridoma cell line M3B was assigned Accession No. DSM ACC2811.

Time-Resolved Immunofluorescence Assays:

Buffers and other solutions used in the assays were either purchased from Wallac, Oy (Turku, Finland) or made from highly purified reagents according to recipes recommended by Wallac. Thus, Assay Buffer was either purchased from Wallac or made as a solution comprising 50 mM Tris-HCl/154 mM NaCl/20 µM diethylenetriaminepentaacetic acid/0.01% (w/v) Tween 40/0.5% (w/v) BSA/0.05% (w/v) NaN$_3$, pH 7.8 and Wash Buffer was either purchased from Wallac or made as a solution comprising 5 mM Tris-HCl/154 mM NaCl/0.005% (w/v) Tween 20/0.1% Germall II, pH 7.8. Stabilizer Solution and Enhancement Solution were purchased from Wallac. Aspiration and wash steps were performed using a DELFIA® Research model 1296-024 plate washer (Wallac) and fluorescence measurements were made with a DELFIA® Research model 1 2 3 4 fluorimeter (Wallac) with excitation at 320 nm, emission at 615 nm and a pulse rate of 1000/second. Fluorescence was measured for 400 µs between flashes after a delay of 400 µs. The microtiter plates employed were of the MaxiSorp FluoroNunc™ brand (Nunc A/S, Roskilde, Denmark) in a 96-well format. Purified polyclonal mouse IgG was purchased from Pierce Chemical Co. (Rockford, Ill., USA). Purified human prothrombin (1 mg) was labelled with the europium (Eu$^{3+}$) chelate of N$^1$-(p-isothiocyanotobenzyl)-diethylenetriamine-N$^1$,N$^2$,N$^3$,N$^3$-tetraacetic acid (DTTA) using a DELFIA® Eu-Labelling kit (Wallac) and the labelled protein purified according to the manufacturer's instructions. The labelled human prothrombin (Eu-hPT) was stored in Stabilizer Solution at −70° C. Based on titration experiments, an antibody concentration of 20 µg/ml for the coating step and a concentration of Eu-hPT of 1.5 nM were chosen, producing a fluorescence intensity in the assays (in the absence of competitor) of up to ~450,000 cps. The background fluorescence measured for controls wells coated with purified polyclonal mouse IgG (ImmunoPure® mouse IgG; Pierce Chemical Co., Rockford, Ill., USA) was always less than 2000 cps. Background values were subtracted before plotting the data. For the label-binding step in the assays, stock solutions of Eu-labelled proteins, competitor proteins, antibodies, and samples of plasma and conditioned cell culture medium were diluted in Assay Buffer.

Figure 2:
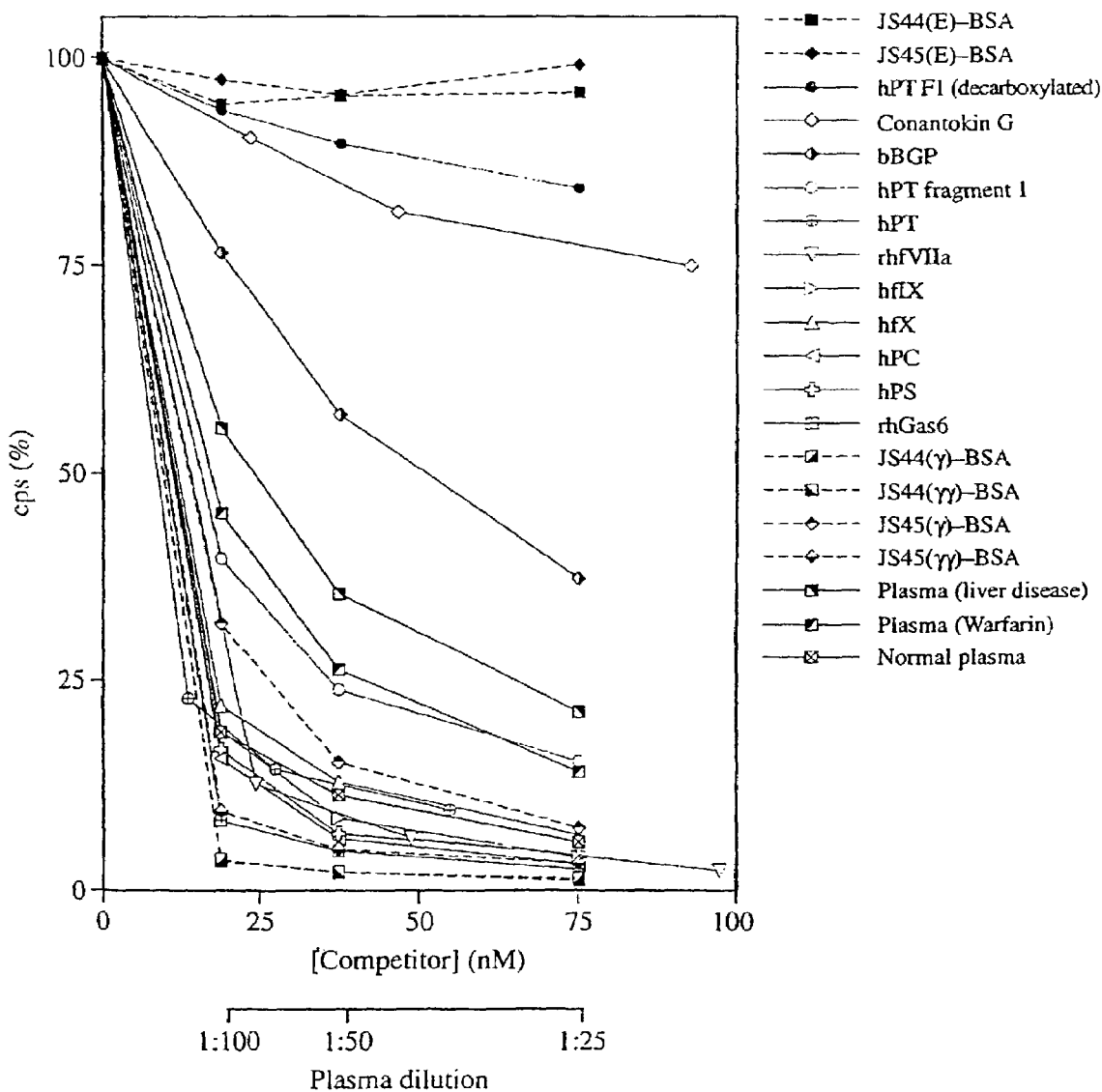

Competitive Immunofluorescence Assay:

Competitive immunofluorescence assays were used to measure the crossreactivities of immobilised anti-Gla monoclonal antibodies towards proteins presented in solution. Purified competitor proteins were as described above under "Western blot analysis". Purified anti-Gla monoclonal antibodies or polyclonal mouse IgG were diluted in TBS to a concentration of 20 µg/ml and added to microtiter plates (50 µl per well). After incubating the plates overnight at 4° C., the solution was removed from the wells and unoccupied binding sites were blocked by adding Assay Buffer (300 µl per well) and gently shaking the plates at room temperature for 2 hours. The Assay Buffer was removed by aspiration, the plates washed two times with Wash Buffer, and 100 µl per well of 1.5 nM Eu-hPT premixed with various concentrations of competitor proteins or various dilutions of human plasma or conditioned cell culture medium was added to the plates. Control wells received 100 µl of 1.5 nM Eu-hPT in the absence of a competitor. The plates were shaken gently at room temperature for 1 hour, then the solutions were removed by aspiration, the plates washed four times, and Enhancement Solution was added (200 µl per well). The plates were gently vortexed for 5 minutes and the fluorescence intensity of the samples measured. As an example, the results obtained with monoclonal antibody M3B are shown in FIG. 2 and demonstrate that the antibody binds a wide range of Gla-containing proteins and peptides. In addition, the degree of inhibition observed for plasma from a patient undergoing treatment with Warfarin® (a vitamin K antagonist that inhibits γ-carboxylation) and plasma from a patient with liver disease was markedly lower than that observed for normal human plasma.

Thus, the anti-Gla antibodies may prove useful for assessing the γ-carboxylation status of proteins in plasma samples. Results for each of the seven groups of anti-Gla monoclonal antibodies are given in Table 3.

The assay proved to be a sensitive method for detecting Gla-containing proteins. As demonstrated in FIG. 2, the lowest amounts tested for the mammalian Gla-containing proteins (1.3-1.9 pmoles) were easily detectable by the assay and the sensitivity is probably considerably greater than this. Even so, the assay is (at least 50 times) more sensitive than standard amino acid sequence analysis.

Figure 3:
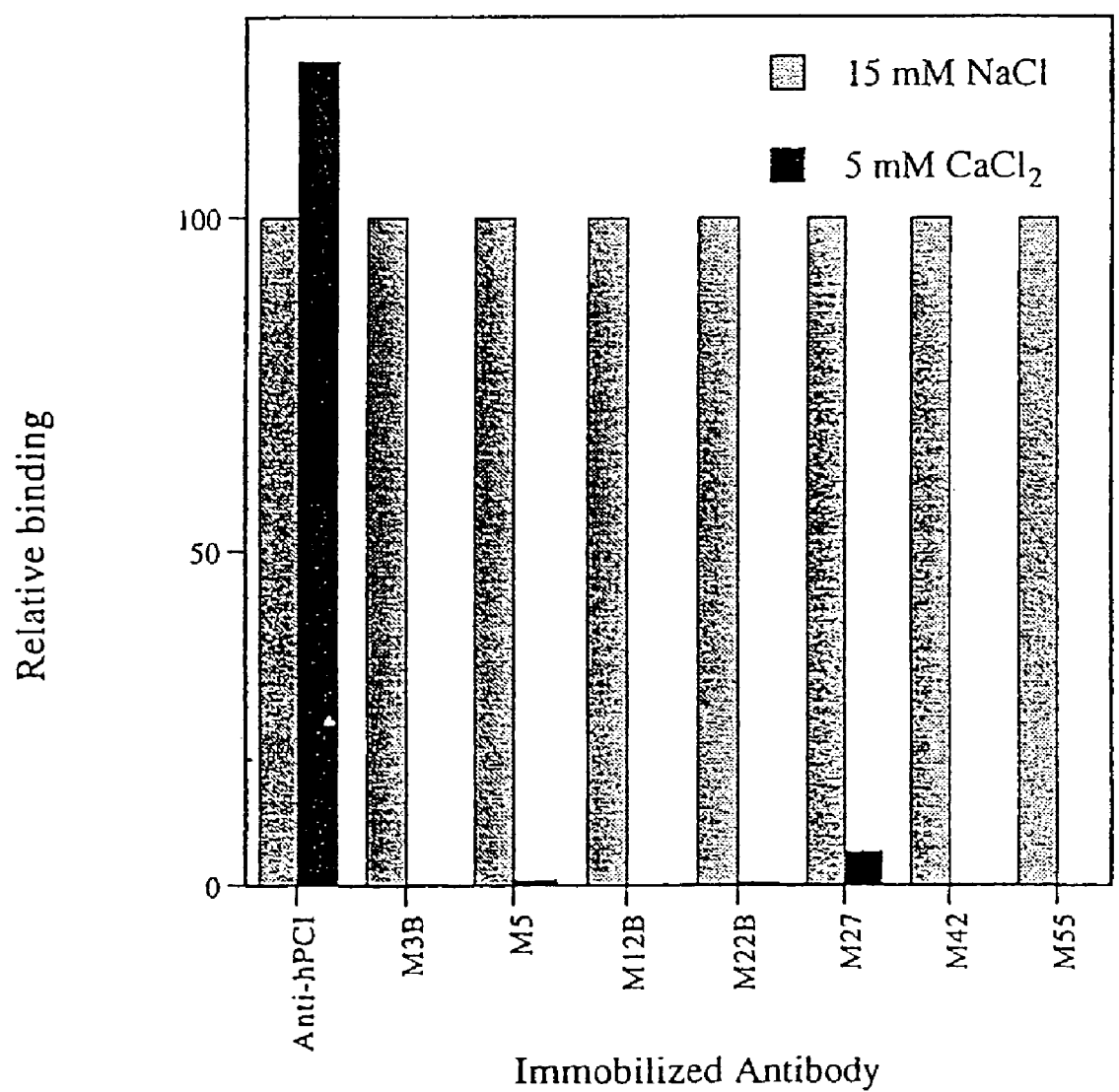

Non-Competitive Immunofluorescence Assay:

Ca$^{2+}$ ions were shown to strongly inhibit the binding of human prothrombin to the anti-Gla antibodies by employing a non-competitive immunofluorescence assay. Purified anti-Gla monoclonal antibodies, purified mouse monoclonal anti-human protein C inhibitor antibody, and polyclonal mouse IgG were each diluted in TBS to a concentration of 20 µg/ml and added to microtiter plates (50 µl per well). After incubating the plates overnight at 4° C., the solution was removed from the wells and unoccupied binding sites were blocked by adding Assay Buffer (300 µl per well) and gently shaking the plates at room temperature for 5 hours. The Assay Buffer was removed by aspiration, the plates washed two times with Wash Buffer, and 1.5 nM Eu-hPT or 1.5 nM Eu-labelled human protein C inhibitor was added to appropriate wells (100 µl per well). Each labelled protein had been prepared in Assay Buffer supplemented with either 5 mM CaCl$_2$ or 15 mM NaCl (to maintain an equivalent ionic strength). The plates were shaken gently at room temperature for 2 hours, then the solutions were removed by aspiration, the plates were washed four times, and Enhancement Solution was added (200 µl per well). The plates were gently vortexed for 5 minutes and the fluorescence intensity of the samples measured. Results for each of the seven groups of anti-Gla monoclonal antibodies are shown in FIG. 3. The strong inhibition of binding observed in the presence of 5 mM CaCl$_2$ is consistent with studies demonstrating that in the presence of Ca$^{2+}$ ions, prothrombin adopts a conformation in which the Gla residues are folded into the interior of the Gla domain and are therefore largely inaccessible to the solvent (Soriano-Garcia et al., 1992; Sunnerhagen et al., 1995).

Crossover Immunofluorescence Assay:

Purified anti-Gla monoclonal antibodies and polyclonal mouse IgG were diluted in TBS to a concentration of 20 µg/ml and added to microtiter plates (50 µl per well). After incubating the plates overnight at 4° C., the solution was removed from the wells and unoccupied binding sites were blocked by adding Assay Buffer (300 µl per well) and gently shaking the plates at room temperature for 2 hours. The Assay Buffer was removed by aspiration, the plates were washed two times with Wash Buffer, and 100 µl per well of 1.5 nM Eu-hPT that had been pre-incubated for 30 minutes with 50 µg/ml competitor antibody was added to the plates. Control wells received 100 µl of 1.5 nM Eu-hPT in the absence of a competitor antibody or 100 µl of 1.5 nM Eu-hPT that had been pre-incubated for 30 minutes with 50 µg/ml polyclonal mouse IgG. The plates were shaken gently at room temperature for 1 hour, then the solutions were removed by aspiration, the plates washed four times, and Enhancement Solution was added (200 µl per well). The plates were gently vortexed for 5 minutes and the fluorescence intensity of the samples measured. Based on the results of this assay, seven distinct patterns of inhibition were observed for the anti-Gla monoclonal antibodies (Table 2).

Figure 4:
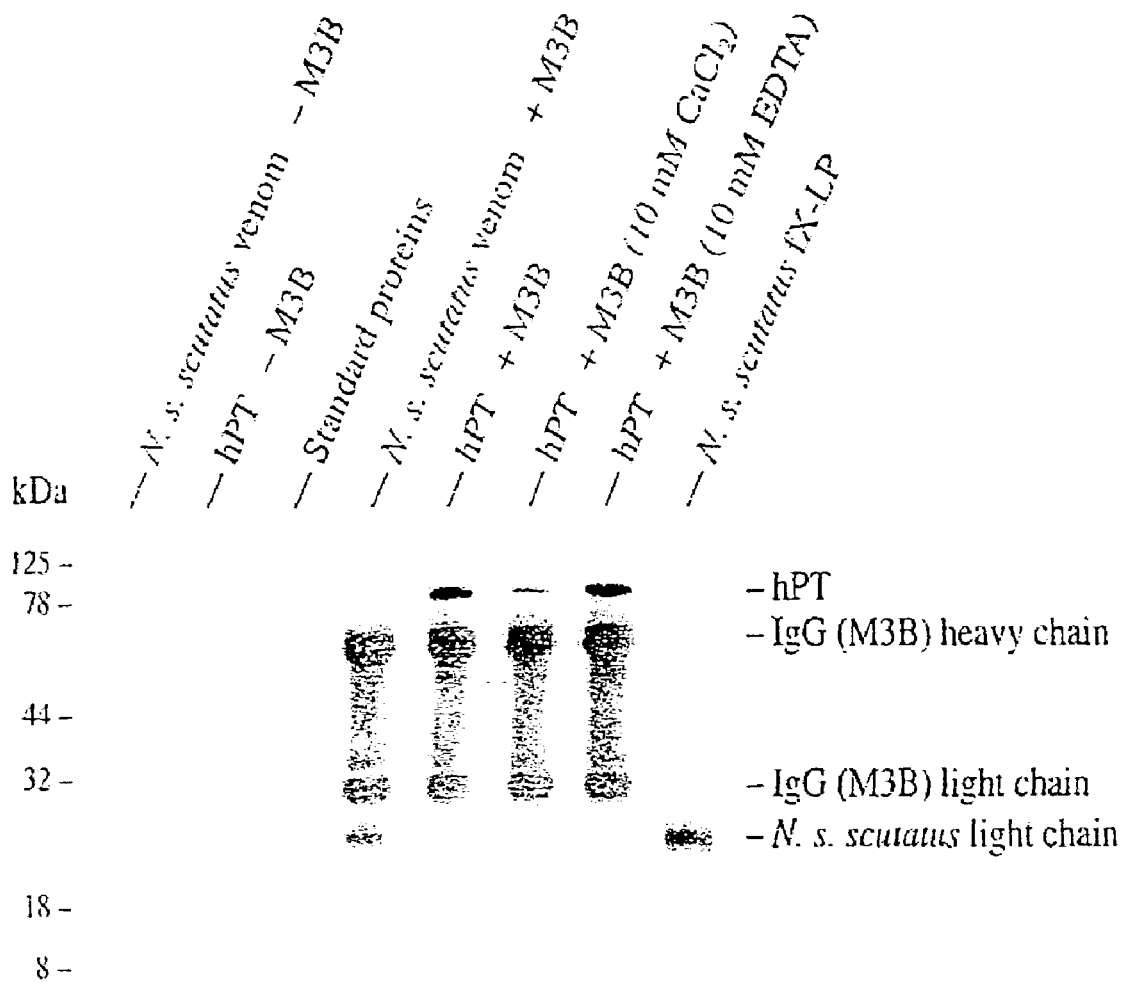

Immunoprecipitation of Gla-Containing Proteins:

Monoclonal antibody M3B was shown to be an effective agent for isolating a Gla-containing protein from a complex biological sample by immunoprecipitation, as demonstrated by immunoprecipitation of tiger snake (*Notechis scutatus scutatus*) factor $X_a$-like protein from venom (FIG. 4). Lyophilized venom from *N. s. scutatus* (Sigma Chemical Co., St. Louis, Mo., USA) was dissolved in 20 mM Tris-HCl/154 mM NaCl, pH 7.4 (Tris Buffered Saline; TBS) to give a final concentration of venom of 1 mg/ml. A 25-µl aliquot of the dissolved venom (25 µg) was mixed in a tube with 5 µl (5 µg) purified monoclonal antibody M3B (1 mg/ml in TBS). As a negative control, 5 µl TBS was added to a 25-µl aliquot of venom (25 µg) instead of the antibody. As a control, purified human prothrombin (~2.2 µg) was mixed with 5 µg purified monoclonal antibody M3B in separate tubes in solutions comprising either TBS, TBS/10 mM $CaCl_2$, or TBS/10 mM EDTA (total volume 30 µl). A negative control, in which the antibody was omitted, comprised purified human prothrombin (2.2 µg) in TBS (total volume 30 µl). The samples were incubated at room temperature for 90 minutes on a shaking platform. During this time, ImmunoSorba® Protein A-coupled beads (Excorin® KB, Lund, Sweden) were prepared. The beads were resuspended by gentle vortexing and a 100 µl-aliquot was mixed with 500 µl TBS/T (TBS containing 0.2% Tween 20), centrifuged briefly, and the supernatant discarded. This step was repeated and the beads were finally resuspended in 600 µl TBS/T. After the 90-minute sample incubation was complete, 100 µl of the resuspended beads was added to each of the above reactions and the samples were incubated at room temperature for three hours with gentle shaking. The reactions were then centrifuged for 5 minutes at 10,000 g and the supernatant was removed by aspiration and discarded. The beads were washed by resuspending them in 400 µl TBS/T, centrifuging the samples for 5 minutes at 10,000 g and discarding the supernatant. The wash step was repeated two more times. Protein that had remained bound to the beads was released by adding 25 µl of 15.6 mM Tris-HCl/0.5% (w/v) SDS/2.5% (v/v) glycerol, pH 6.8 containing 1.25% (v/v) β-mercaptoethanol and 0.0003% (w/v) bromophenol blue and heating the samples at 85° C. for 10 minutes. The samples were then centrifuged for 10 minutes at 20,000 g and the proteins in the supernatant were resolved by electrophoresis in a SDS/12% (w/v) polyacrylamide gel using the discontinuous system of Laemmli (1970). Reference proteins (Kaleidoscope Prestained Standards; Bio-Rad Laboratories AB, Sundbyberg, Sweden) were also electrophoresed. The proteins were electroblotted to Immobilon™-P membrane (Millipore AB, Sundbyberg, Sweden) and Gla-containing polypeptides detected by western blotting using monoclonal antibody M3B and alkaline phosphatase-conjugated rabbit anti-mouse IgG (DAKO A/S, Glostrup, Denmark) as described above under "Western blot analysis".

Purification of Tiger Snake (*N. s. scutatus*) Factor $X_a$-Like Protein by Immunoaffinity Chromatography:

Immunoaffinity chromatography using an anti-Gla monoclonal antibody coupled to a chromatographic resin was observed to be a selective, rapid and mild method to isolate Gla-containing proteins from complex biological fluids, as was demonstrated by isolating the factor $X_a$-like protein from venom of *N. s. scutatus* by chromatography on monoclonal M3B-coupled resin with an elution step employing 50 mM $CaCl_2$.

Unless stated otherwise, all procedures were performed at room temperature. To prepare an immunoaffinity resin, monoclonal antibody M3B (100 mg) was dialysed into Oxidation Buffer (20 mM sodium acetate buffer/0.5 M NaCl, pH 5) and concentrated to a volume of 2.5 ml. To the sample was added 50 µl 0.5 M sodium meta-periodate (to oxidise carbohydrate moieties on the antibody) and the solution was shaken gently in the dark for 1 hour at room temperature. The oxidation reaction was terminated by the addition of 125 µl glycerol and the sample was exchanged into Coupling Buffer (0.1 M sodium acetate buffer/1 M NaCl, pH 4.9) by chromatography on a PD-10 gel filtration column (Amersham Pharmacia Biotech AB, Uppsala, Sweden). The sample (3.5 ml volume) was added to 9 ml (drained bed volume) UltraLink Immobilized Hydrazide resin (Pierce Chemical Co., Rockford, Ill., USA) and incubated at 4° C. for 14 hours. The resin was washed with 30 ml Oxidation Buffer and this was used to estimate the coupling efficiency by spectrophotometry according to the resin manufacturer's instructions. Coupling efficiency was estimated to be 97%. The resin was stored in 20 mM Tris-HCl/0.5 M NaCl, pH 7.4 containing 0.05% (w/v) $NaN_3$ at 4° C. before use.

An aliquot of the monoclonal antibody M3B-coupled resin was used to prepare an immunoaffinity column with a settled bed volume of 3.5 ml and the column was equilibrated in Binding Buffer (19 mM Tris-HCl/146 mM NaCl/10 mM EDTA, pH 7.4). Lyophilized tiger snake (*N. s. scutatus*) venom (10 mg; Sigma Chemical Co., St. Louis, Mo., USA) was dissolved in 2.5 ml Binding Buffer and chromatographed on a PD-10 gel filtration column (Amersham Pharmacia Biotech AB, Uppsala, Sweden) that had been pre-equilibrated with Binding Buffer. The venom preparation was loaded onto the immunoaffinity column at a flow rate of 0.5 ml/min and the absorbance at 280 nm ($A_{280}$) of the effluent was monitored. After the $A_{280}$ decreased to near the baseline level the column was washed with 19 mM Tris-HCl/354 mM NaCl/10 mM EDTA, pH 7.4 at a flow rate of 2 ml/min. Protein bound to the column was eluted with 19 mM Tris-HCl/146 mM NaCl/50 mM $CaCl_2$, pH 7.4 (FIG. 5A). The $Ca^{2+}$-eluted fraction was dialysed into TBS and stored at −20° C.

The flowthrough fraction (protein that did not bind to the resin during loading) and the $Ca^{2+}$-eluted fraction were examined by SDS-PAGE and western blot analysis (FIGS. 5B and C). The purified protein comprised two subunits (termed the "light" and "heavy" chains) as judged by SDS-PAGE under reducing conditions (FIG. 5B). Only the light chain, which is expected to contain a Gla domain similar to that of mammalian hemostatic proteins such as factor X, was recognised by monoclonal antibody M3B (FIG. 5C) and the other anti-Gla monoclonal antibodies (Table 3). The flowthrough fraction did not crossreact with monoclonal antibody M3B on western blots (FIG. 5C), indicating that most or all of the factor $X_a$-like protein had been bound by the immunoaffinity resin with high efficiency during a single passage through the column.

The protein isolated from *N. s. scutatus* venom by immunoaffinity chromatography was conclusively identified as the Gla-containing protein, *N. s. scutatus* factor $X_a$-like protein, by the following criteria:

1. The subunit structure of the isolated protein (i.e. comprising a light chain and heavy chain) matched that reported for the Gla-containing *N. s. scutatus* factor $X_a$-like protein purified by other researchers using alternative methods (size exclusion and ion-exchange chromatography steps) (Tans et al., 1985) (FIG. 5B).

2. N-terminal amino acid sequence analysis of the light chain of the isolated protein (10 residues) produced the sequence S-N-S-L-F-γ-γ-I-R-P (SEQ ID NO:1) (where γ denotes a Gla residue) that contained two Gla residues. The sequence was identical to that reported for the N-terminus of the light chain of the factor Xa-like protein (prothrombin activator) isolated from the venom of another closely related elapid snake, *Tropidechis carinatus* (Joseph et al., 1999).

For N-terminal amino acid sequence analysis, the immunoaffinity-purified protein was reduced with dithiothreitol and alkylated with iodoacetamide using standard procedures. The heavy and light chain polypeptides were separated by SDS-PAGE, electroblotted to ProBlott™ membrane (Applied Biosystems, Inc., Stockholm, Sweden), and the polypeptides detected with Coomassie Blue R-250 stain. The band representing the light chain polypeptide was excised from the membrane and cut in two. One half was used for N-terminal sequence analysis without further modification by employing Edman degradation chemistry and an ABI Protein Sequencer (Perkin-Elmer Corp., Stockholm, Sweden). This produced the sequence S-N-S-L-F-X-X-I-R-P (SEQ ID NO:2) (where X indicates that no distinct signal was observed, as would be expected if a posttranslationally modified amino acid such as Gla was present at these positions).

Before commencing sequence analysis using the other half of the membrane, the membrane was first treated with methanolic HCl in the amino acid sequencer in situ to methylesterify Gla residues, thus allowing them to be detected during sequence analysis. Following this treatment, the sequence S-X-X-L-F-γ-γ-I (SEQ. ID NO:3) (where y denotes a Gla residue) was obtained.

FIGURE LEGENDS

FIG. 1. Crossreactivity of monoclonal antibody M3B towards western-blotted proteins. Protein samples (~0.5 μg each) that had been denatured and reduced were electrophoresed in a SDS/12% (w/v) polyacrylamide gel (except for bovine bone Gla protein, for which 3 μg protein and a 15% gel were used because of its small molecular mass; 5.8 kDa). The proteins were electroblotted to ProBlott™ membrane and incubated sequentially with monoclonal antibody M3B and alkaline phosphatase-conjugated rabbit anti-mouse IgG. The western blot was developed using BCIP/NBT substrate solution. Abbreviations used in the figure are as follows: hPT, human prothrombin (containing 10 Gla residues); hPT fragment 1, a fragment of human prothrombin comprising residues 1-156 of the mature protein (10 Gla); hPT fragment 1 (decarboxylated), hPT fragment 1 that had been heat-treated to convert Gla residues to Glu; hfvII, human factor VII (10 Gla); hfIx, human factor IX (12 Gla); hfX, human factor X (11 Gla); hPC, human protein C (9 Gla); hPS, human protein S (11 Gla); rhGas6, conditioned cell culture medium containing recombinant human growth arrest-specific protein 6 (hGas6 derived from plasma contains 11 Gla residues); JS44 (γ)-BSA, JS45(γ)-BSA, JS44(E)-BSA and JS45(E)-BSA, BSA-conjugated synthetic peptides containing a single Gla (γ) residue or a Glu (E) residue at the corresponding position (see Table 1). Bovine bone Gla protein or osteocalcin (bBGP) contains three Gla residues and is indicated on the far right of the figure. Monoclonal M3B crossreacted only with the Gla-containing proteins and peptides and not with decarboxylated hPT fragment 1, JS44(E)-BSA or JS45(E)-BSA. For the proteins comprising two subunits (a heavy and a light chain, i.e. hfX and hPC), only the light chain containing the Gla domain was recognised.

FIG. 2. Competitive immunofluorescence assay demonstrating the crossreactivity of immobilised monoclonal antibody M3B towards proteins in solution. Purified monoclonal antibody M3B was coated onto the wells of microtiter plates at a concentration of 20 μg/ml (50 μl per well) overnight at 4° C. Unoccupied binding sites in the wells were blocked by adding Assay Buffer (300 μl per well) and gently shaking the plates at room temperature for 2 hours. The Assay Buffer was removed by aspiration, the plates were washed two times with Wash Buffer, and 100 μl per well of 1.5 nM Eu-hPT that had been premixed with various concentrations of competitor proteins or various dilutions of human plasma or conditioned cell culture medium was added to the plates. Control wells received 100 μl of 1.5 nM Eu-hPT in the absence of a competitor. After incubation at room temperature for 1 hour with gentle shaking, the solutions were removed by aspiration, the plates washed four times, and Enhancement Solution was added (200 μl per well). The plates were gently vortexed for 5 minutes and the fluorescence intensity (counts per second or cps) of the samples measured. The cps values measured in the absence of a competitor were defined as 100%. Data values are the average obtained from duplicate samples. The proteins and peptides listed in the figure legend are as follows: decarboxylated hPT fragment 1 (a fragment comprising residues 1-156 of human prothrombin (hPT) that had been heat-treated to destroy the majority of the Gla residues), conantokin G (a 17-amino acid peptide from cone snail venom that contains 5 Gla residues), bBGP (bovine bone Gla protein or osteocalcin; 3 Gla residues), hPT fragment 1 (10 Gla residues), hPT (full-length hPT; 10 Gla residues), rhfVIIa (recombinant activated human factor VII; 10 Gla residues are present in plasma-derived hfvII), hfIX (human factor IX; 12 Gla residues), hfX (human factor X; 11 Gla residues), hPC (human protein C; 9 Gla residues), hPS (human protein S; 11 Gla residues), rhGas6 (conditioned cell culture medium containing recombinant human growth arrest-specific protein 6; 11 Gla residues are present in plasma-derived Gas6). The six BSA-coupled peptides (JS44 and JS45 series), containing 1 and 2 Gla residues or Glu at the corresponding positions, are described in Table 1.

FIG. 3. Inhibitory effect of $Ca^{2+}$ on the binding of human prothrombin to immobilised anti-Gla monoclonal antibodies. Purified anti-Gla monoclonal antibodies and purified mouse monoclonal anti-human protein C inhibitor antibody were coated onto the wells of microtiter plates at a concentration of 20 μg/ml (50 μl per well) overnight at 4° C. Unoccupied binding sites in the wells were blocked by adding Assay Buffer (300 μl per well) and gently shaking the plates at room temperature for 5 hours. The Assay Buffer was removed by aspiration, the plates were washed two times with Wash Buffer, and 1.5 nM Eu-hPT or 1.5 nM Eu-labelled human protein C inhibitor were added to appropriate wells (100 μl per well). Each labelled protein had been prepared in Assay Buffer supplemented with either 5 mM $CaCl_2$ or 15 mM NaCl (to maintain an equivalent ionic strength). The plates were shaken gently at room temperature for 2 hours, then the solutions were removed by aspiration, the plates washed four times, and Enhancement Solution was added (200 μl per well). The plates were gently vortexed for 5 minutes and the fluorescence intensity (counts per second or cps) of the samples measured. The cps value measured in the absence of $Ca^{2+}$ was given an arbitrary value of 100 and the fluorescence measured in the presence of $Ca^{2+}$ was plotted relative to this value. Data values are the average obtained from duplicate samples.

FIG. 4. Immunoprecipitation of Gla-containing proteins by monoclonal antibody M3B. Tiger snake (*Notechis scutatus scutatus*) venom (25 μg) or human prothrombin (hPT, 2.2 μg) were incubated for 90 minutes with 51 g monoclonal antibody M3B (refer to lanes labelled +M3B) in various buffered solutions (TBS, TBS containing 10 mM $CaCl_2$, or TBS containing 10 mM EDTA). Controls from which the antibody was omitted were also performed (refer to lanes labelled –M3B). Protein A-coupled beads were added to the samples and after a 3-hour incubation, the beads were washed thoroughly. The antibody-antigen complexes that had bound to the beads were eluted and Gla-containing polypeptides were detected by western blot analysis using monoclonal antibody M3B and alkaline phosphatase-conjugated rabbit anti-mouse IgG. The lane on the far right of the figure contained a control sample comprising *N. s. scutatus* factor $X_a$-like protein ($fX_a$-LP) isolated by barium-citrate precipitation according to standard procedures (Stocker et al., 1994). Bands corresponding to hPT and the light chain of the snake $fX_a$-LP protein are clearly evident in the immunoprecipitated samples. As would be expected, immunoprecipitation of hPT was inhibited by the addition of $CaCl_2$.

Figure 5:
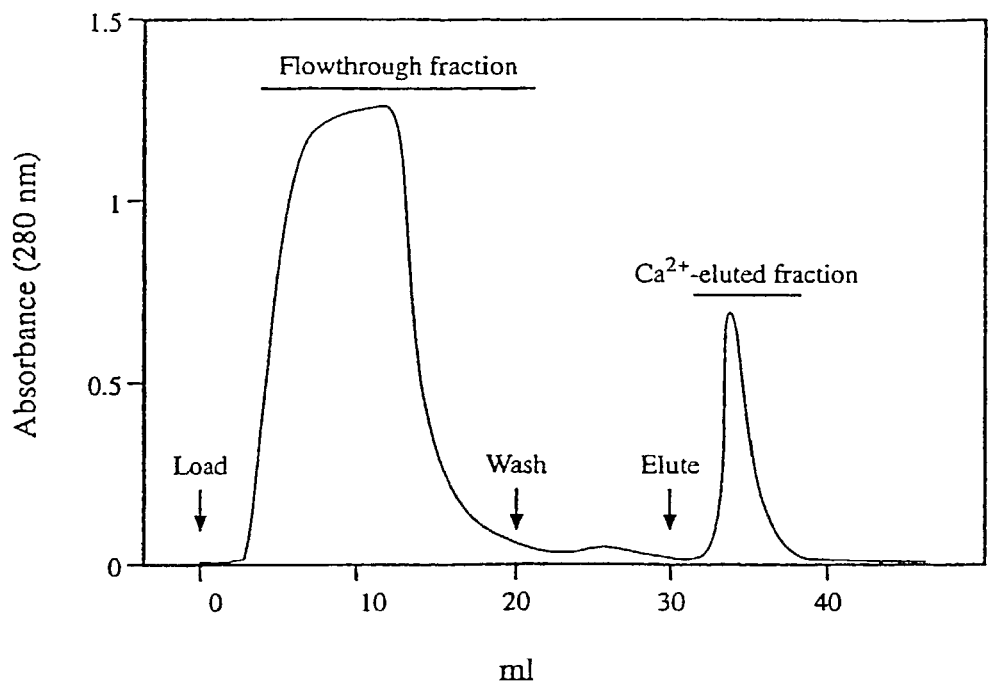
Figure 5:
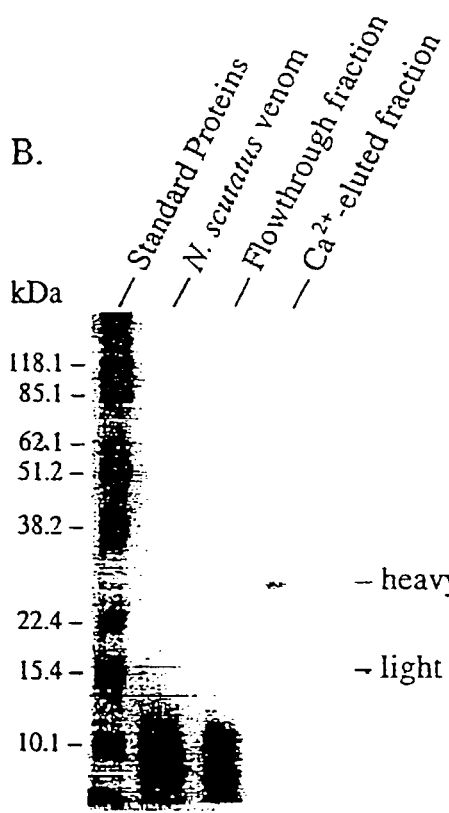
Figure 5:
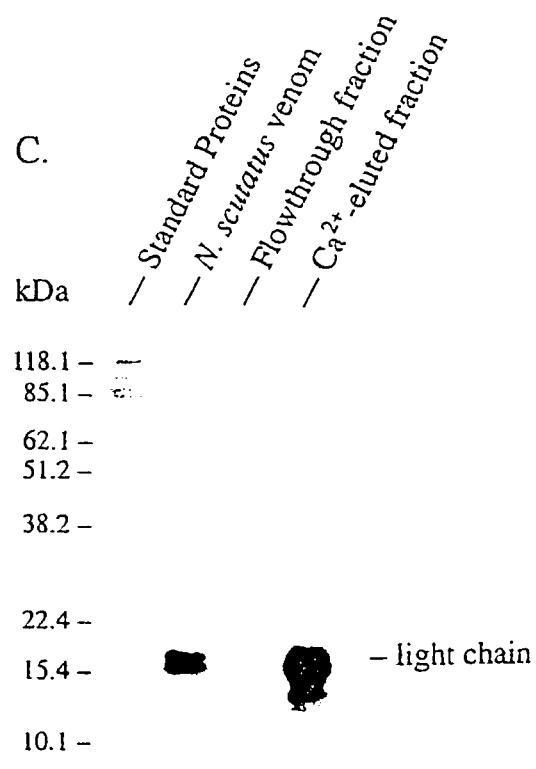

FIG. 5. Purification of tiger snake factor $X_a$-like protein by immunoaffinity chromatography. Monoclonal antibody M3B was covalently attached to UltraLink Immobilised Hydrazide resin and a column with a settled bed volume of 3.5 ml was prepared and equilibrated in Binding Buffer (19 mM Tris-HCl/146 mM NaCl/10 mM EDTA, pH 7.4). Lyophilized tiger snake (*Notechis scutatus scutatus*) venom (10 mg; Sigma Chemical Co.) was dissolved in 2.5 ml Binding Buffer and chromatographed on a PD-10 gel filtration column to reduce the $Ca^{2+}$ concentration in the preparation. The venom preparation was loaded onto the immunoaffinity column (A) at a flow rate of 0.5 ml/min and when the $A_{280\ nm}$ had returned almost to the baseline level the column was washed with 19 mM Tris-HCl/354 mM NaCl/10 mM EDTA, pH 7.4 at a flow rate of 2 ml/min. Protein bound to the column was eluted with 19 mM Tris-HCl/146 mM NaCl/50 mM $CaCl_2$, pH 7.4. The flowthrough and $Ca^{2+}$-eluted fractions (shown by bars) were collected separately for analysis. Aliquots of the gel-filtrated venom preparation and the flowthrough and $Ca^{2+}$-eluted fractions collected during immunoaffinity chromatography were denatured and reduced and duplicate samples were electrophoresed in a SDS/12% (w/v) polyacrylamide gel. After electrophoresis, the gel was cut into two pieces and the proteins in one section were detected by staining with Coomassie Blue R-250 dye (B). Proteins in the other gel section were electroblotted to ProBlott™ membrane and incubated sequentially with monoclonal antibody M3B and alkaline phosphatase-conjugated rabbit anti-mouse IgG. The Western blot (C) was developed using BCIP/NBT substrate solution.

TABLE 1

A. Synthetic peptides

| Peptide | Amino acid sequence[1] | |
|---|---|---|
| JS30 | $NH_2$-K A D γ D A F A γ A A L A γ γ A D A-COOH | (SEQ ID NO:4) |
| | G I F G G D G D Q G D G | (SEQ ID NO:5) |
| | K K G K Q I H G S H I L | (SEQ ID NO:6) |
| | L L I L S K K I V K Q Q | (SEQ ID NO:7) |
| | T L L T V T P N Y L S V | (SEQ ID NO:8) |
| | T S Y T Y | (SEQ ID NO:9) |
| | V V | (SEQ ID NO:10) |
| JS31 | $NH_2$-KAAγAAAAγAAAAγγAAAKKC-COOH | (SEQ ID NO:11) |
| JS32 | $NH_2$-KAAEAAAAEAAAAEEAAAKKC-COOH | (SEQ ID NO:12) |
| JS44 (γ) | $NH_2$-LTGKγLTGDC-COOH | (SEQ ID NO:13) |
| JS44 (E) | $NH_2$-LTGKELTGDC-COOH | (SEQ ID NO:14) |
| JS44 (γγ) | $NH_2$-LTGKγγLTGDC-COOH | (SEQ ID NO:15) |
| JS45 (γ) | $NH_2$-ASRVγTAFGC-COOH | (SEQ ID NO:16) |
| JS 45 (E) | $NH_2$-ASRVETAFGC-COOH | (SEQ ID NO:17) |
| JS45 (γγ) | $NH_2$-ASRVγγTAFGC-COOH | (SEQ ID NO:18) |

[1]Amino acid sequences are given in single-letter code.
γ-Carboxyglutamyl residues are denoted by γ.

TABLE 2

1. Classification of monoclonal antibodies by various methods

| | Antibody | | | | | | |
|---|---|---|---|---|---|---|---|
| Method | M3B | M76 | M12B | M5 M5B a) | M17 M22B Group | M27 M52 M42 | M24 M47 M54 M55 M57 M69 |
| IgG subclass analysis | 2 bκ | 1 κ | 1 κ | 1 κ | 1κ | 3 κ | 1 κ |
| Agarose gel electrophoresis | A | b | c | d | e | f | E |
| SDS-PAGE | A | A | A | A | B | A | A |
| Western blots | I | ii | ii | ii | iii | ii | Iv |
| Competitive immunoassays | I | II | III | IV | V | VI | VII |

TABLE 2-continued

1. Classification of monoclonal antibodies by various methods

| Method | M3B | M5<br>M5B<br>M76 | M12B | M17<br>M22B<br>a) | M27<br>M52<br>Group | M42 | M24<br>M47<br>M54<br>M55<br>M57<br>M69 |
|---|---|---|---|---|---|---|---|
| Crossover immunoassays | I | II | III | IV | V | VI | VII |
| Overall group | 1 | 2 | 3 | 4 | 5 | 6 | 7 |

The 16 monoclonal antibodies were grouped according to their IgG subclass, mobility in agarose and SDS-polyacrylamide gels, and crossreactivities as determined by western blot analysis and competitive and crossover immunofluorescence assays. Seven groups were distinguished based on these characteristics.

The degree of crossreactivity exhibited by the monoclonal antibodies in western blot and competitive immunofluorescence assays was scored as either strong (+), weak (+/−) or undetectable (−).

N.d., not determined.

REFERENCES

Bajaj, S. P. and Birktoft, J. J. (1993) Human factor IX and factor IXa. Methods in Enzymology 222, 96-128

Bajaj, S. P., Price, P. A. and Russell, W. A. (1982) Decarboxylation of γ-carboxyglutamic acid residues in human prothrombin: stoichiometry of calcium binding to γ-carboxyglutamic acid in prothrombin. Journal of Biological Chemistry 257, 3726-3731

Borrebäck, C. A. K. and Eylar, M. E. (1981) Production and characterisation of a monoclonal antibody against the second seed lectin of the *Dolichos biflorus* plant. Journal of Biological Chemistry 256, 4723-4725

TABLE 3

(1) Crossreactivities of monoclonal antibodies

| Antigen | M3B (1) | M5 (2) | M12B (3) | M22B (4) | M27 (5) | M42 (6) | M55 (7) |
|---|---|---|---|---|---|---|---|
| *Western blot analysis* | | | | | | | |
| hPT | + | + | + | + | + | + | + |
| hPT F1 | + | + | + | + | + | + | + |
| hPTFI (decarboxylated) | − | − | − | − | − | − | − |
| hFVII | + | + | + | + | + | + | + |
| rhFVIIa | + | + | + | + | + | + | + |
| hFIX | + | + | + | + | + | + | + |
| hFIXa | + | + | + | + | + | + | + |
| hFX | + | + | + | + | + | + | + |
| hPC | + | − | − | − | + | − | +/− |
| hPS | + | + | + | + | + | + | + |
| rhGas6 | + | + | + | + | + | + | + |
| Black snake $FX_a$-LP | + | + | + | + | + | + | + |
| Taipan $FX_a$-LP | + | + | + | + | + | + | + |
| Tiger snake $FX_a$-LP | + | + | + | + | + | + | + |
| bBGP | + | − | − | − | − | − | − |
| JS44 (γ) = BSA | + | + | + | + | − | + | − |
| JS44 (E) - BSA | − | − | − | − | − | − | − |
| JS44 (γ γ) - BSA | + | + | + | + | − | + | − |
| JS45 (γ) - BSA | + | + | + | + | − | + | − |
| JS45 (E) - BSA | − | − | − | − | − | − | − |
| JS45 (γ γ) - BSA | + | + | + | + | − | + | − |
| *Immunofluorescence assay* | | | | | | | |
| hPT | + | + | + | + | + | + | + |
| hPT F1 | + | + | +/− | + | + | + | + |
| hPTFI (decarboxylated) | − | − | − | − | − | − | − |
| rhFVIIa | + | + | + | + | + | + | + |
| hFIX | + | + | + | + | + | + | + |
| hFX | + | + | + | + | + | n.d. | + |
| hPC | + | + | +/− | + | + | +/− | + |
| hPS | + | + | + | + | + | + | + |
| rhGas6 | + | + | + | + | + | + | + |
| Conantokin G | +/− | + | +/− | − | + | n.d. | + |
| JS44 (γ) = BSA | + | + | + | + | +/− | + | − |
| JS44 (E) - BSA | − | − | − | − | − | − | − |
| JS44 (γ γ) - BSA | + | + | + | + | − | + | − |
| JS45 (γ) - BSA | + | + | + | + | − | + | − |
| JS45 (E) - BSA | − | − | n.d. | n.d. | n.d. | n.d. | n.d. |
| JS45 (γ γ) - BSA | + | + | + | + | +/− | + | − |

Cairns, J. R., Williamson, M. K. and Price, P. A. (1991) Direct identification of γ-carboxyglutamic acid in the sequencing of vitamin K-dependent proteins. Analytical Biochemistry 199, 93-97

Frackelton, A. R., Jr., Ross, A. H. and Eisen, H. N. (1983) Characterization and use of monoclonal antibodies for isolation of phosphotyrosyl proteins from retrovirus-transformed cells and growth factor-stimulated cells. Molecular and Cellular Biology 3, 1343-1352

Furie, B., Bouchard, B. A. and Furie, B. C. (1999) Vitamin K-dependent biosynthesis of γ-carboxyglutamic acid. Blood 93, 1798-1808

Jie, K. -S. G., Gijsbers, B. L. M. G. and Vermeer, C. (1995) A specific calorimetric staining method for γ-carboxyglutamic acid-containing proteins in polyacrylamide gels. Analytical Biochemistry 224, 163-165

Joseph, J. S., Chung, M. C. M., Jeyaseelan, K. and Kini, R. M. (1999) Amino acid sequence of Trocarin, a prothrombin activator from *Tropidechis carinatus* venom: its structural similarity to coagulation factor Xa. Blood 94, 621-631

Kulman, J. D., Harris, J. E., Haldeman, B. A. and Davie, E. W. (1997) Primary structure and tissue distribution of two novel proline-rich γ-carboxyglutamic acid proteins. Proceedings of the National Academy of Sciences of the United States of America 94, 9058-9062

Laemmli, U. K. (1970) Cleavage of structural proteins during the assembly of the head of bacteriophage T4. Nature 227, 680-685

Nishimoto, S. K. (1990) A calorimetric assay specific for γ-carboxyglutamic acid-containing proteins: its utility in protein purification procedures. Analytical Biochemistry 186, 273-279

Olivera, B. M., Rivier, J., Clark, C., Ramilo, C. A., Corpuz, G. P., Abogadie, F. C., Mena, E. E., Woodward, S. R., Hillyard, D. R. and Cruz, L. J. (1990) Diversity of *Conus* neuropeptides. Science 249, 257-263

Persson, E., Selander, M., Linse, S., Drakenberg, T., Ohlin, A. K. and Stenflo, J. (1989) Calcium binding to the isolated β-hydroxyaspartic acid-containing epidermal growth factor-like domain of bovine factor X. Journal of Biological Chemistry 264, 16897-16904

Price, P. A. (1984) Decarboxylation of γ-carboxyglutamic acid residues in proteins. Methods in Enzymology 107, 548-551

Rigby, A. C., Lucas-Meunier, E., Kalume, D. E., Czerwiec, E., Hambe, B., Dahlqvist, I., Fossier, P., Baux, G., Roepstorff, P., Baleja, J. D., Furie, B. C., Furie, B. and Stenflo, J. (1999) A conotoxin from *Conus textile* with unusual posttranslational modifications reduces presynaptic $Ca^{2+}$ influx. Proceedings of the National Academy of Sciences of the United States of America 96, 5758-5763

Soriano-Garcia, M., Padmanabhan, K., de Vos, A. M. And Tulinsky, A. (1992) The $Ca^{2+}$ ion and membrane binding structure of the Gla domain of Ca-prothrombin fragment 1. Biochemistry 31, 2554-2566

Stenflo, J. and Dahlbäck, B. (1994) Vitamin K-dependent proteins. In The Molecular Basis of Blood Diseases, Stamatoyannopoulos, G., Nienhuis, A. W., Majerus, P. W. and Varmus, H., ed., W. B. Saunders Co., Philadelphia, pp. 565-598

Stocker, K., Hauer, H., Moller, C. and Triplett, D. A. (1994) Isolation and characterization of Textarin®, a prothrombin activator from eastern brown snake (*Pseudonaja textilis*) venom. Toxicon 32, 1227-1236

Sunnerhagen, M., Forsén, S., Hoffrén, A. M., Drakenberg, T., Teleman, O. and Stenflo, J. (1995) Structure of the $Ca^{2+}$-free Gla domain sheds light on membrane binding of blood coagulation proteins. Nature Structural Biology 2, 504-509

Suttie, J. W. (1985) Vitamin K-dependent carboxylase. Annual Review of Biochemistry 54, 459-477

Tam, J. P. (1988) Synthetic peptide vaccine design: synthesis and properties of a high-density multiple antigenic peptide system. Proceedings of the National Academy of Sciences of the United States of America 85, 5409-5413

Tans, G., Govers-Riemslag, J. W. P., van Rijn, J. L. M. L. and Rosing, J. (1985) Purification and properties of a prothrombin activator from the venom of *Notechis scutatus scutatus*. Journal of Biological Chemistry 260, 9366-9372

Vermeer, C. and De Boer-Van den Berg, M. A. (1985) Vitamin K-dependent carboxylase. Haematologia 18, 71-97

---

The invention claimed is:

1. An isolated anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1, which antibody is a polyclonal antibody.

2. An isolated anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1, said antibody further comprises a label.

3. The antibody of claim 2 wherein the label is covalently attached to the antibody.

4. The antibody of claim 2 wherein the label is an enzyme, a fluorescent compound or a radioactive compound.

5. The antibody of claim 1 or 2, which is a mouse antibody, rat antibody, rabbit antibody, horse antibody, cow antibody, goat antibody, chicken antibody or a sheep antibody.

6. The antibody of claim 5 wherein said antibody is derived from a Balb/c mouse.

7. The antibody of claim 1 or 2 wherein the protein or the peptide comprises the amino acid sequence of SEQ ID NO:1.

8. The antibody of claim 1 or 2 wherein the protein or the peptide is a bone Gla protein or a matrix Gla protein.

9. The antibody of claim 1 or 2 wherein the antibody binds to two adjacent Gla residues.

10. A purified monoclonal antibody M3b Accession No. DSM ACC 2811.

11. A method of making an anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1, said method comprises:
   (i) immunizing an animal with: (i) peptides containing one or more Gla residues; or (ii) a multiple antigen peptide system containing a peptide, comprising one or more Gla residues;
   (ii) screening for said antibody which specifically binds one or more γ-carboxyglutamic acid in a protein and does not specifically bind to a glutamic acid residue in a protein; and
   (iii) isolation of said antibody.

12. The method of claim 11 wherein the molecule comprises a peptide containing one or more amino acid sequences of SEQ ID NOS: 4, 5, 6, 7, 8, 9, and 10.

13. The method according to claim 11, wherein said animal is a mouse, a rat, a rabbit, a horse, a cow, a goat, a chicken or a sheep.

14. The method of claim 13 wherein the mouse is a Balb/c mouse.

15. A method of detecting or quantifying a Gla-containing protein in a sample, said method comprising:
   (i) contacting the sample with an anti-Gla antibody, wherein said antibody specifically binds one or more γ-carboxyglutamic acid (Gla) residues in a protein or a peptide, and wherein said antibody specifically binds a Gla-containing peptide of Table 1 but which does not specifically bind to a corresponding glutamic acid (Glu)-containing peptide of Table 1 such that said antibody binds a Gla-containing protein in said sample; and
   (ii) detecting or quantifying the binding of said antibody to the Gla-containing protein in said sample wherein the sample is a biological fluid, a tissue extract, or a tissue specimen, and wherein the sample is in a blot.

16. The method of claim 15 wherein the blot is a western blot.

17. A method of detecting or quantifying a Gla-containing protein in a sample, said method comprising:
   (i) contacting the sample with an anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1 such that said antibody binds a Gla-containing protein in said sample; and
   (ii) detecting or quantifying the binding of said antibody to the Gla-containing protein in said sample, wherein the Gla-containing protein is contained in the venom of molluscs of the genus *Conus*.

18. The method of claim 17 wherein the Gla-containing protein is conantokin G.

19. A method of measuring the degree of carboxylation of a vitamin K-dependent coagulation factor in a sample from a subject, said method comprises:
   (i) contacting the sample with an anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1, such that said antibody binds a Gla-containing vitamin K-dependent coagulation factor; and
   (ii) quantifying said binding of said antibody to the Gla-containing vitamin K-dependent coagulation factor.

20. The method of claim 19 wherein the degree of carboxylation of the vitamin K-dependent coagulation factor is monitored during treatment of the subject with a vitamin K-antagonistic drug.

21. The method of claim 20 wherein the vitamin K-antagonistic drug is WARFARIN®.

22. A method of purifying a recombinant Gla-containing protein from lysed cells or cell culture media containing the recombinant Gla-containing protein, the method comprising:
   (i) contacting the lysed cells or cell culture media with an anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1 such that said antibody binds said recombinant Gla-containing protein to form an antibody bound recombinant Gla-containing protein and
   (ii) separating said antibody bound recombinant Gla-containing protein from the lysed cells or cell culture media.

23. The method of claim 22 wherein the bound recombinant Gla-containing protein is separated from the lysed cells or cell culture media by an immunoaffinity chromatography or by immunoprecipitation.

24. The method of claim 22 wherein the recombinant Gla-containing protein is a bone Gla protein or a matrix Gla protein.

25. A method of immunoaffinity fractionating Gla-containing proteins according to the Gla content of the Gla-containing proteins, the method comprising:

(i) contacting the Gla-containing protein with an anti-Gla antibody, wherein said antibody specifically binds one or more γ-carboxyglutamic acid (Gla) residues in a protein or a peptide, and wherein said antibody specifically binds a Gla-containing peptide of Table 1, but which does not specifically bind to a corresponding glutamic acid (Glu)-containing peptide of Table 1, so that the Gla-containing proteins bind to the antibody;

(ii) removing unbound proteins; and (iii) eluting the Gla-containing proteins of a specific Gla-content bound to the antibody.

26. The method of claim 25 wherein the eluting of the bound proteins is performed using a buffer comprising metal ions.

27. The method of claim 26 wherein the metal ions are calcium ions.

28. The method of claim 25 wherein the eluting of the Gla-containing proteins is performed by a change in pH-value or by the addition of chaotropic agents.

29. A method of screening for a cation that affects the conformation of a Gla-domain of a Gla-containing protein, said method comprising:

(i) contacting a Gla-containing protein with an anti-Gla antibody, wherein said antibody specifically binds one or more y-carboxyglutamic acid (Gla) residues in a protein or a peptide. and wherein said antibody specifically binds a Gla-containing peptide of Table 1, but which does not specifically bind to a corresponding glutamic acid (Glu)-containing peptide of Table 1, in the presence of the cation; and (ii) detecting binding of said antibody to the Gla-containing protein wherein binding of the antibody to the Gla-containing protein indicates that the cation does not have an effect on the conformation of the Gla-containing protein, and non-binding of the Gla-containing protein to the antibody indicates that the cation has an effect on the conformation of the Gla-containing protein.

30. The method of claim 29 wherein the cation is Calcium ion.

31. An isolated anti-Gla antibody which specifically binds one or more Gla residues in a protein or a peptide, wherein said antibody specifically binds a plurality of Gla-containing proteins or peptides of Table 3 but which does not specifically bind corresponding Glu-containing proteins or peptides wherein the antibody exhibits an Overall Group (2), (3), (4), (5), (6), or (7) crossreactivity of Table 3.

32. A hybridoma line that produces the monoclonal antibody M3b Accession No. DSM ACC 2811.

* * * * *

SEQUENCE LISTING

```
<160> NUMBER OF SEQ ID NOS: 18

<210> SEQ ID NO 1
<211> LENGTH: 10
<212> TYPE: PRT
<213> ORGANISM: N.s. scutatus
<220> FEATURE:
<221> NAME/KEY: VARIANT
<222> LOCATION: 6,7
<223> OTHER INFORMATION: Xaa = Gla residue
<220> FEATURE:
<223> OTHER INFORMATION: N-terminal amino acid sequence analysis of the
      light chain of the isolated protein from N.s. scutatus venom.

<400> SEQUENCE: 1

Ser Asn Ser Leu Phe Xaa Xaa Ile Arg Pro
 1               5                   10

<210> SEQ ID NO 2
<211> LENGTH: 10
<212> TYPE: PRT
<213> ORGANISM: N.s. scutatus
```

```
<220> FEATURE:
<221> NAME/KEY: VARIANT
<222> LOCATION: 6,7
<223> OTHER INFORMATION: Xaa = no distinct signal was observed
<220> FEATURE:
<223> OTHER INFORMATION: N-terminal amino acid sequence analysis of
      one-half of the light chain of the isolated protein from N.s.
      scutatus venom.

<400> SEQUENCE: 2

Ser Asn Ser Leu Phe Xaa Xaa Ile Arg Pro
1               5                   10

<210> SEQ ID NO 3
<211> LENGTH: 8
<212> TYPE: PRT
<213> ORGANISM: N.s. scutatus
<220> FEATURE:
<221> NAME/KEY: VARIANT
<222> LOCATION: 2,3
<223> OTHER INFORMATION: Xaa = no distinct signal was observed
<220> FEATURE:
<221> NAME/KEY: VARIANT
<222> LOCATION: 6,7
<223> OTHER INFORMATION: Xaa = Gla residue
<223> OTHER INFORMATION: N-terminal amino acid sequence analysis of the
      light chain of the isolated protein from N.s. scutatus venom.

<400> SEQUENCE: 3

Ser Xaa Xaa Leu Phe Xaa Xaa Ile
1               5

<210> SEQ ID NO 4
<211> LENGTH: 18
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa = Carboxyglutamyl residues
<220> FEATURE:
<223> OTHER INFORMATION: Synthetic peptide used to produce monoclonal
      antibodies

<400> SEQUENCE: 4

Lys Ala Asp Xaa Asp Ala Phe Ala Xaa Ala Ala Leu Ala Xaa Xaa Ala
1               5                   10                  15

Asp Ala

<210> SEQ ID NO 5
<211> LENGTH: 18
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa = Carboxyglutamyl residues
<220> FEATURE:
<223> OTHER INFORMATION: Synthetic peptide used to produce monoclonal
      antibodies

<400> SEQUENCE: 5

Lys Gly Ile Xaa Phe Gly Gly Asp Xaa Gly Asp Gln Gly Xaa Xaa Asp
1               5                   10                  15

Gly Ala

<210> SEQ ID NO 6
<211> LENGTH: 18
<212> TYPE: PRT
```

```
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 6

Lys Lys Lys Xaa Gly Lys Gln Ile Xaa His Gly Ser His Xaa Xaa Ile
 1               5                  10                  15

Leu Ala

<210> SEQ ID NO 7
<211> LENGTH: 18
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 7

Lys Leu Leu Xaa Ile Leu Ser Lys Xaa Lys Ile Val Lys Xaa Xaa Gln
 1               5                  10                  15

Gln Ala

<210> SEQ ID NO 8
<211> LENGTH: 18
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 8

Lys Thr Leu Xaa Leu Thr Val Thr Xaa Pro Asn Tyr Leu Xaa Xaa Ser
 1               5                  10                  15

Val Ala

<210> SEQ ID NO 9
<211> LENGTH: 18
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 9

Lys Ala Thr Xaa Ser Ala Phe Ala Xaa Tyr Ala Leu Thr Xaa Xaa Tyr
 1               5                  10                  15

Asp Ala

<210> SEQ ID NO 10
<211> LENGTH: 18
```

```
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 10

Lys Ala Val Xaa Val Ala Phe Ala Xaa Ala Ala Leu Ala Xaa Xaa Ala
1               5                   10                  15

Asp Ala

<210> SEQ ID NO 11
<211> LENGTH: 21
<212> TYPE: PRT
<213> ORGANISM: Artificial Sequence
<220> FEATURE:
<221> NAME/KEY: VARIANT
<222> LOCATION: 4, 9, 14, 15
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 11

Lys Ala Ala Xaa Ala Ala Ala Ala Xaa Ala Ala Ala Ala Xaa Xaa Ala
1               5                   10                  15

Ala Ala Lys Lys Cys
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic peptide used to produce monoclonal
      antibodies

<400> SEQUENCE: 12

Lys Ala Ala Glu Ala Ala Ala Ala Glu Ala Ala Ala Ala Glu Glu Ala
1               5                   10                  15

Ala Ala Lys Lys Cys
            20

<210> SEQ ID NO 13
<211> LENGTH: 10
<212> TYPE: PRT
<213> ORGANISM: Artificial Sequence
<220> FEATURE:
<221> NAME/KEY: VARIANT
<222> LOCATION: 5
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 13

Leu Thr Gly Lys Xaa Leu Thr Gly Asp Cys
1               5                   10

<210> SEQ ID NO 14
<211> LENGTH: 10
<212> TYPE: PRT
<213> ORGANISM: Artificial Sequence
<220> FEATURE:
```

```
<223> OTHER INFORMATION: Synthetic peptide used to produce monoclonal
      antibodies

<400> SEQUENCE: 14

Leu Thr Gly Lys Glu Leu Thr Gly Asp Cys
 1               5                  10

<210> SEQ ID NO 15
<211> LENGTH: 11
<212> TYPE: PRT
<213> ORGANISM: Artificial Sequence
<220> FEATURE:
<221> NAME/KEY: VARIANT
<222> LOCATION: 5, 6
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 15

Leu Thr Gly Lys Xaa Xaa Leu Thr Gly Asp Cys
 1               5                  10

<210> SEQ ID NO 16
<211> LENGTH: 10
<212> TYPE: PRT
<213> ORGANISM: Artificial Sequence
<220> FEATURE:
<221> NAME/KEY: VARIANT
<222> LOCATION: 5
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 16

Ala Ser Arg Val Xaa Thr Ala Phe Gly Cys
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide used to produce monoclonal
      antibodies

<400> SEQUENCE: 17

Ala Ser Arg Val Glu Thr Ala Phe Gly Cys
 1               5                  10

<210> SEQ ID NO 18
<211> LENGTH: 11
<212> TYPE: PRT
<213> ORGANISM: Artificial Sequence
<220> FEATURE:
<221> NAME/KEY: VARIANT
<222> LOCATION: 5, 6
<223> OTHER INFORMATION: Xaa= Carboxyglutamyl residues
<220> FEATURE:
<223> OTHER INFORMATION: Synthetic peptide used to produce monoclonal
      antibodies

<400> SEQUENCE: 18

Ala Ser Arg Val Xaa Xaa Thr Ala Phe Gly Cys
 1               5                  10
```